(12) United States Patent
De Luca et al.

(10) Patent No.: US 7,897,584 B2
(45) Date of Patent: Mar. 1, 2011

(54) TAXANES COVALENTLY BOUNDED TO HYALURONIC ACID OR HYALURONIC ACID DERIVATIVES

(75) Inventors: Gilda De Luca, Padua (IT); Rinaldo Marini Bettolo, Rome (IT); Luisa Maria Migneco, Rome (IT)

(73) Assignee: Fidia Farmaceutici S.p.A., Abano Terme (IT)

( * ) Notice: Subject to any disclaimer, the term of this patent is extended or adjusted under 35 U.S.C. 154(b) by 452 days.

(21) Appl. No.: 10/531,853

(22) PCT Filed: Oct. 10, 2003

(86) PCT No.: PCT/EP03/11239

§ 371 (c)(1),
(2), (4) Date: Apr. 18, 2005

(87) PCT Pub. No.: WO2004/035629

PCT Pub. Date: Apr. 29, 2004

(65) Prior Publication Data

US 2006/0116346 A1    Jun. 1, 2006

(30) Foreign Application Priority Data

Oct. 18, 2002    (IT) .......................... PD2002A0271

(51) Int. Cl.
*A61K 31/728* (2006.01)
*C08B 37/00* (2006.01)
(52) U.S. Cl. .......................................... 514/54; 536/53
(58) Field of Classification Search .................. 514/54, 514/53; 536/53
See application file for complete search history.

(56) References Cited

U.S. PATENT DOCUMENTS

| 4,851,521 A | 7/1989 | DeLuca et al. ............. 536/55.1 |
| 5,502,081 A | 3/1996 | Kuo et al. ....................... 514/777 |
| 5,648,506 A * | 7/1997 | Desai et al. .................. 549/510 |
| 5,977,163 A * | 11/1999 | Li et al. ....................... 514/449 |

FOREIGN PATENT DOCUMENTS

WO    WO9733552    9/1997

OTHER PUBLICATIONS

Luo et al Bioconjugate Chem. 1999, 10, 755-763.*
Sparer et al Controlled Release Delivery Systems, Chapter 6, 1983, 107-119.*
Luo et al., "Synthesis and Selective Cytotoxicity of a Hyaluronic Acid-Antitumor Bioconjugate", *Bioconjugate Chem*, vol. 10, pp. 755-763 (1999).
Sparer et al, "Controlled Release from Glycosaminoglycan Drug Complexes", Chapter 6, in *Controlled Release Delivery Systems*, New York (1983).
Akima et al., "Evaluation of Antitumor Activities of Hyaluronate Binding Antitumor Drugs: Synthesis, Characterization and Antitumor Activity", Journal of Drug Targeting, vol. 4, pp. 1-8, 1996.
Denizot et al., "Rapid Colorimetric Assay for Cell Growth and Survival Modifications to the Tetrazolium Dye Procedure Giving Improved Sensitivity and Reliability", Journal of Immunological Methods, vol. 89, pp. 271-277 (1986).
Andrea Herrera Gayol et al, "Effect of Hyaluronan on Xenotransplanted Breast Cancer", Experimental and Molecular Pathology, vol. 72, pp. 179-185 (2002).
Luo et al., "A Hyaluronic Acid-Taxol Antitumor Bioconjugate Targeted to Cancer Cells", Biomacromolecules, vol. 1, pp. 208-218 (2000).
Li et al., "Complete Regression of Well-Established Tumors Using a Novel Water Soluble Poly (L-Glutamic Acid)-Paclitaxel Conjugate", Cancer Research, vol. 58, pp. 2404-2409, (1998).
Mellado et al., "Preparation and Biological Activity of Taxol Acetates", Biochemical and Biophysical Research Communications, vol. 124, No. 2, pp. 329-336 (1984).
Huizing et al., "Taxanes: A New Class of Antitumor Agents", Cancer Investigation, vol. 13, pp. 381-404 (1995).
Manfredi et al., "Taxol Binds to Cellular Microtubules", The Journal of Cell Biology, vol. 94, pp. 688-696, (1982).
Weiss et al., "Hypersensitivity Reactions From Taxol", Journal of Clinical Oncology, vol. 8, No. 7, pp. 1263-1268 (1990).
Nuijen et al., "Progress in the Development of Alternative Pharmaceutical Formulations of Taxanes", Investigational New Drugs, vol. 19, pp. 143-153, (2001).
Robert W. Pfeifer et al., "Precipitation of Paclitaxel During Infusion by Pump", Am J. Hospital Pharmacology, vol. 50, p. 2518, (1993).

* cited by examiner

*Primary Examiner* — Shaojia Anna Jiang
*Assistant Examiner* — Ganapathy Krishnan
(74) *Attorney, Agent, or Firm* — Abelman, Frayne & Schwab

(57) ABSTRACT

The present invention relates to water-soluble taxanes covalently bounded to hyaluronic acid or hyaluronic acid derivatives, and in particular to paclitaxel and docetaxel, useful for the preparation of pharmaceutical compositions to be used in the field of oncology, in the treatment of autoimmune disorders and of restenoisis. The invention also relates to the process for preparing taxanes covalently bounded to hyaluronic acid or hyaluronic acid derivatives by direct synthesis between molecules of hyaluronic acid and of taxane or by indirect synthesis by the introduction of a spacer between the hyaluronic acid or hyaluronic acid derivative and the taxane.

32 Claims, 4 Drawing Sheets

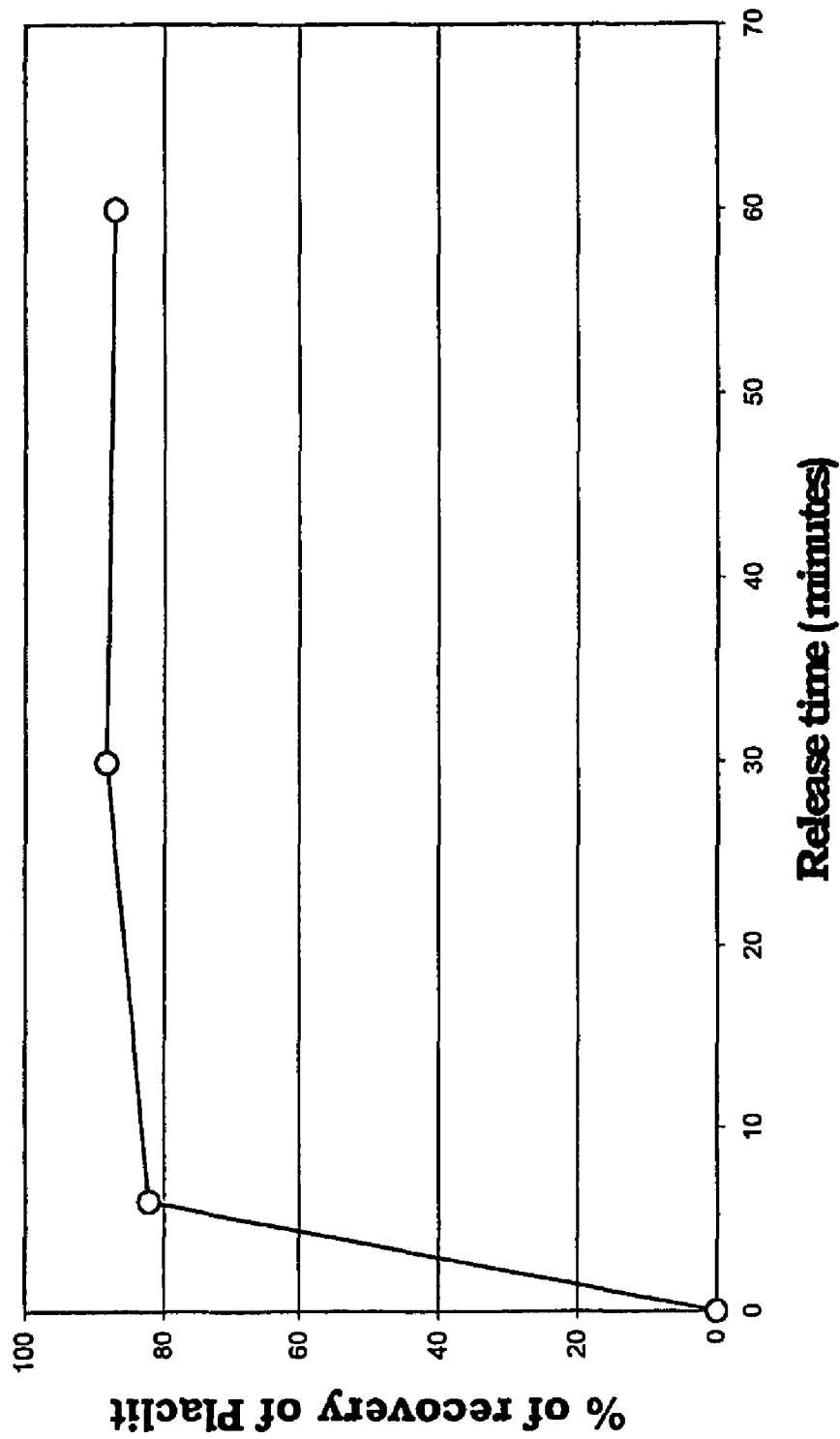

TAXANES COVALENTLY BOUNDED TO HYALURONIC ACID OR HYALURONIC ACID DERIVATIVES

FIELD OF THE INVENTION

The present invention relates to taxanes, in particular paclitaxel and docetaxel, covalently bounded to hyaluronic acid or hyaluronic acid derivatives, to the process for their preparation and to their use in the field of oncology, in the treatment of autoimmune disorders and restenosis.

STATE OF THE ART

Taxanes, and in particular paclitaxel and docetaxel, currently marketed under the trade names Taxol® and Taxotere®, are anticancer agents (Huizing M. T. et al., *Cancer Inv.*, 1995, 13: 381-404) that exert their antiproliferative effect by acting on the organisation of the microtubules in the cellular cytoskeletal system. Indeed, by inhibiting the depolarisation of said microtubules, they prevent their normal dynamic reorganisation that occurs during mitotic cell division (Manfredi J. J. et al., *J. Cell Biol.*, 1982, 94: 688-696).

The main therapeutic indications for paclitaxel are:
therapy for advanced breast cancer;
therapy for Kaposi's sarcoma;
therapy for carcinoma of the lung (not microcytoma)
carcinoma of the ovary, resistant to standard chemotherapy treatment.

Moreover, said chemotherapy is also used to treat carcinoma of the bladder, prostate and endometrium.

Given that paclitaxel is insoluble in water, it is mixed with Cremophor® EL (castor oil)—ethyl alcohol in a ratio of 1:1, in the pharmaceutical compositions currently used in cancer chemotherapy (Pfeifer R. W. et al., *Am. J. Hosp. Pharm.*, 1993, 50:2520-2521). This formulation is usually used for continuous intravenous infusion (for between 3 and 24 hours) at a dosage of 135-175 mg/m$^2$.

The presence of Cremophor® EL in the above said formulation is the main cause of the adverse reactions that normally occur during administration of paclitaxel, ranging from simple attacks of urticaria to dyspnea and bronchospasm, and even anaphylactic shock (Weiss, R. B. et al., *J. Clin. Oncol.*, 1990, 8: 1263-1268).

For this reason, any patient who is going to receive treatment with a pharmaceutical composition of paclitaxel-Cremophor® EL must first follow a premedication protocol, with the administration of dexamethasone, possibly associated with an antihistamine.

In spite of these precautions, up to 40% of the patients who receive intravenous infusion of paclitaxel still experience more or less severe adverse reactions. It can therefore be said that the formulation of Taxol® currently in clinical use, and the methods used for administering it, constitute a limitation to its efficacy. This is the reason why research is now being directed towards the synthesis of new pharmaceutical formulations and/or towards new chemical formulations of the above anticancer drug, that are water-soluble.

For instance, researchers have attempted to encapsulate paclitaxel in liposomes, nanocapsules and microspheres constituted by a polymer wall formed by biodegradable co-polymers, such as polylactic acid, and non-biodegradable co-polymers, such as ethylene-vinyl-acetate.

Moreover, microspheres have been prepared that are loaded with paclitaxel formed by a biodegradable polymer, such as polyphosphoester, to create a system for the prolonged release of drug at the treatment site in the therapy for lung carcinoma (Nuijen, B. et al., *Investigational New Drugs*, 2001, 19: 143-153). There have also been attempts to prepare micelles of said anticancer drug by precipitating paclitaxel in an organic solvent with phosphatidylcholine/bile salts (Nuijen, B. et al., *Investigational New Drugs*, 2001, 19: 143-153).

However, these new systems for the encapsulation of paclitaxel may prove troublesome with regard to stability, production and reproducibility.

Moreover, various attempts have been made to dissolve the drug with cyclodextrine, but the new formulations did not give the desired results (Nuijen, B. et al., *Investigational New Drugs*, 2001, 19: 143-153).

Chemical research into new formulations of paclitaxel that render the drug more water-soluble while maintaining its efficacy as an anticancer agent, has led to the synthesis of new analogues modified at the C2$^I$ and C7 position. (US patent application No. 2001/0018531) as well as to the preparation of new prodrugs.

Prodrugs are therapeutically inert drug derivatives that are activated by being introduced into a body. There, after spontaneous hydrolysis and/or enzymatic degradation processes, the active principle is released.

In view of this, and for the above said reasons, many attempts have been made to synthesise new prodrugs which have led, for instance, to the preparation of drugs such as acetyl-paclitaxel (Mellado, W. et al., *Biochem. Blophys. Res. Commun.*, 1984, 124(2): 329-336), or to the synthesis of new esters of said drug with succinic, glutaric and sulphonic acid on the carbon in position C2$^I$. These esters, however, proved to be unstable in aqueous environment.

Moreover, some derivatives with a phosphonoxyphenylpropionate ester group at the C2$^I$ or C7 position have been synthesised, such as paclitaxel-2$^I$-carbonate, and a series of new amino acid esters of paclitaxel and derivatives thereof, with a glutaryl group at position C2$^I$.

Glutaryl-paclitaxel asparagine and glutaryl-paclitaxel glutamine have proved to be the two most highly water-soluble products obtained by the type of synthesis described above, but they are less efficacious than paclitaxel per se (Nuijen, B. et al., *Investigational New Drugs*, 2001, 19: 143-153).

It is also known that paclitaxel has been esterified with poly-L-glutamic acid to form a new water-soluble derivative of said chemotherapy drug, with a significantly higher plasma half-life than non-conjugated paclitaxel (Li C. et al., *Cancer Research*, 1998, 58(11): 2404-2409).

Paclitaxel has also been derivatised with PEG (polyethylene glycol) by esterifying the chemotherapy drug at position C2$^I$; however, the new molecule has proved to be highly water-soluble but not very stable.

Lastly, a new delivery system for the drug has recently been developed, by the conjugation of paclitaxel with human serum albumin (HSA). The paclitaxel-HSA conjugate has proved to be very water-soluble and capable of carrying up to 30 molecules of chemotherapy drug. However, experiments performed in vitro have shown it to be less efficacious against cancer than paclitaxel per se (Nuijen, B. et al., *Investigational New Drugs*, 2001, 19:143-153).

Recently, researchers have synthesized a new delivery system for paclitaxel esterified with previously modified hyaluronic acid (hereinafter referred to as "HA"), that is HA reacted with molecules of hydrazide bound to the carboxyl group of HA by an amide bond (Luo Y. et al., *Biomacromolecules* 2000, 1 (2): 208-218; U.S. Pat. No. 5,874,417). This new delivery system for paclitaxel enables the drug to go directly to the membrane surface of the target cancer cell, characterized by overexpression of the receptor for HA, CD44. Consequently, the paclitaxel bounded to HA functionalized with a hydrazide proves to be able to bind specifically to the CD44 of the cancer cell, and it is thus enabled (thanks to a process of endocytosis) to enter the cell cytoplasm where it can be enzymatically released and activated, triggering its inhibition of the depolarization of tubuline and therefore of cellular division. This mechanism of selective transport of the drug is called "cell targeting".

Moreover, it is known that HA can be used as a vehicle for anticancer drugs in pharmaceutical compositions wherein HA is associated with (and not covalently bound to) chemotherapy drugs, such as paclitaxel, to increase their therapeutic. efficacy thanks to the targeting phenomenon described above (International Patent Application No. WO 00/41730) and to enable the doses commonly specified in normal chemotherapy protocols to be lowered (International Patent Application No. WO 99/02151).

Lastly, low-molecular-weight HA and/or the lipid derivatives thereof are known to be used to prepare liposomes used for the delivery of drugs, including anticancer drugs such as paclitaxel (International Patent Application No. WO 01/39815).

In view of what said above, it is still felt the need of novel taxanes derivatives, which are stable and soluble in water, and therapeutically efficacious at least so as the not-modified taxanes are.

SUMMARY OF THE INVENTION

The Applicant has now found that covalently bounding taxanes to HA or HA derivatives, optionally by means of a spacer, stable and water-soluble products are obtained, useful for the preparation of pharmaceutical compositions for the treatment of tumours, autoimmune disorders and restenosis.

It is therefor subject of the invention a taxane covalently bounded to HA or to a HA derivative, wherein the covalent bond is formed between hydroxyl groups of the taxane and carboxyl groups or hydroxyl groups of HA or of HA derivatives, or amino groups of deacetylated HA, optionally by means of a spacer linking the taxane to HA or HA derivative, with the proviso that the said spacer is different from a hydrazide.

The present invention further relates to the processes for the preparation of taxanes covalently bounded to HA or HA derivatives.

Further subject of the invention are the pharmaceutical compositions comprising as the active substance at least a taxane covalently bounded to HA or HA derivatives, and their use in the treatment of tumours, autoimmune disorders and restenosis.

The present taxanes covalently bounded to HA or HA derivatives have many advantages, which may be summarised as follows:

1) they are instantly soluble in the bloodstream;
2) they do not need to be mixed with Cremophor® El for the preparation of formulations, thus overcoming the aforesaid problems concerning hypersensitivity and anaphylaxis;
3) thanks to the enzymatic action of enzymes such as the esterases commonly present in plasma, the taxanes are instantly released by their vehicle HA or HA derivative from the present compositions into the blood, where they can freely perform their anticancer activity;
4) they enable a new drug to be obtained which, in the case of certain types of cancer, may exert surprising chemotherapy activity that is significantly greater than that obtained when a non-conjugated taxane is administered, when same doses of drug are considered.

BRIEF DESCRIPTION OF THE DRAWINGS

FIG. 4 shows the percentage of paclitaxel covalently bounded to HA ester prepared as described in Example 7, released in human plasma as described in test of Example 13, vs. time.

DETAILED DESCRIPTION OF THE INVENTION

Figure 1:
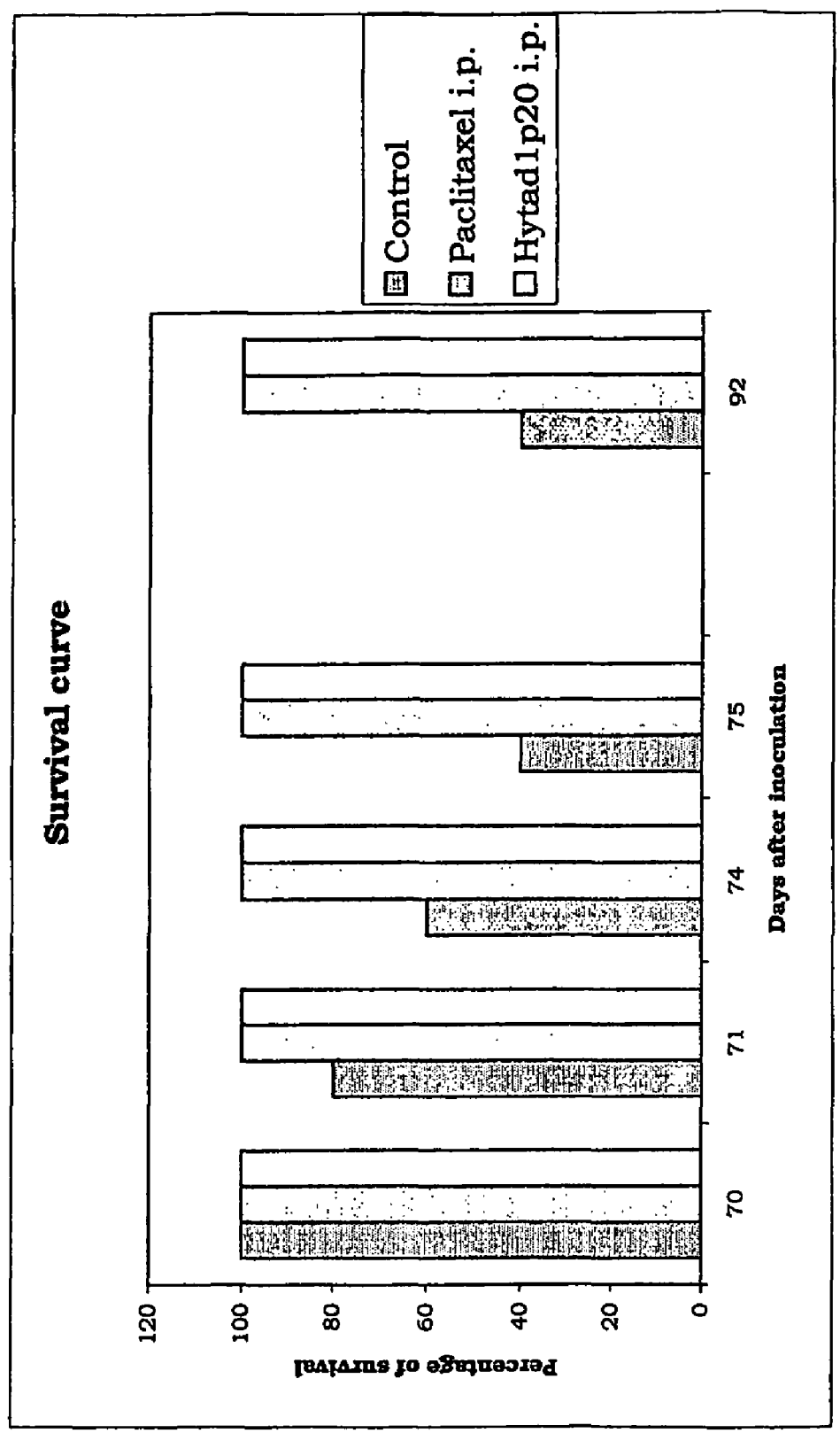
FIG. 1 shows the percentage of survival after implant of neoplastic cells as described in Example 1 for controls (black histogram), and for mice who received paclitaxel (grey histogram), and paclitaxel covalently bounded to HA ester with 16% of esterification (white histogram) prepared as in Example 7.

The present invention describes compounds belonging to the taxane family, preferably paclitaxel and docetaxel hereinafter represented by the formulae (I) and (II) respectively, covalently bounded to HA or HA derivatives, preferably by means of a spacer as an interface between the taxane component and the HA or HA derivative, being covalently bound to both molecules.

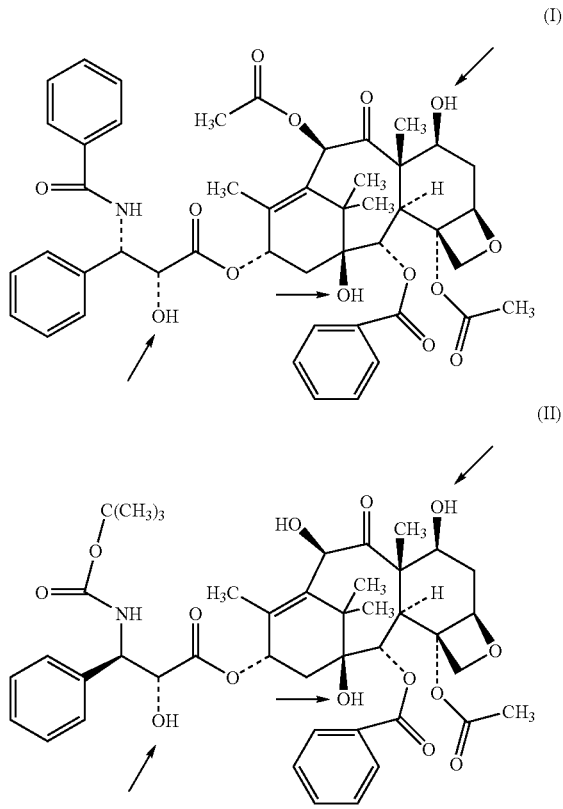

HA is a hetero-polysaccharide composed of alternate residues of D-glucuronic acid and N-acetyl-D-glucosamine, having the following repeating unit:

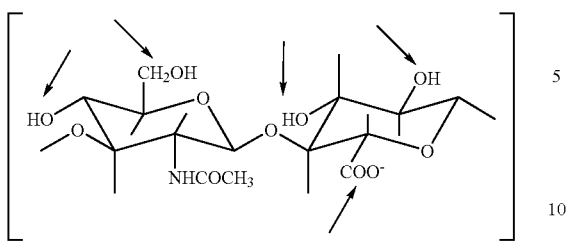

HA is a linear-chain polymer with a molecular weight which may vary between. 50,000 and 13×10⁶ Da, according to its source and the method used to obtain it. It is present in nature in the. pericellular gels, in the fundamental substance of connective tissue in vertebrate organisms (of which it is one of the main components), in the synovial fluid of joints, in the vitreous humor and in the umbilical cord. HA plays an important role in the biological organism, as a mechanical support for the cells of many tissues such as the skin, the tendons, the muscles and the cartilage. It is the main component of the extracellular matrix, but it has other functions, such as the hydration of tissues, lubrication, and cell migration and differentiation.

The HA used in the present invention may be extracted from any source, for example from cocks' combs, or it may be obtained by the fermentation route, or by technological means, and it may have a molecular weight of between 400 and 3×10⁶ Da, in particular between 400 and 1×10⁶ Da, and preferably, between 400 and 230,000 Da.

The HA derivatives according to the present invention are preferably selected from the group consisting of the following HA derivatives:

HA salified with organic and/or inorganic bases;

Hyaff®: HA esters with alcohols of the aliphatic, araliphatic; cycloaliphatic, aromatic, cyclic and heterocyclic series, with an esterification degree that may vary according to the type and length of the alcohol used, and is in any case never over 50% esterification, and preferably between 0.1 and 20% since the final polymer that is obtained must always be water-soluble, while the remaining percentage of non-esterified HA may be salified with organic and/or inorganic bases, disclosed in U.S. Pat. No. 4,851,521 incorporated herewith by reference;

Hyadd™: amides of HA with amines of the aliphatic, araliphatic, cycloaliphatic, aromatic, cyclic and heterocyclic series, with a percentage of amidation of between 0.1 and 10%, since the final polymer must always be water-soluble, while the remaining percentage of HA that is not amidated can be salified with organic and/or inorganic bases, disclosed in European patent application No. 1095064 incorporated herewith by reference;

O-sulphated HA derivatives to the 4th degree of sulphation, disclosed in U.S. Pat. No. 6,027,741 incorporated herewith by reference;

ACP®: inner esters of HA with a percentage of esterification of no more than 15%, as the polymer must always be water-soluble, preferably between 0.05 and 10% of esterification, while the remaining percentage of unesterified HA can be salified with organic and/or inorganic bases, disclosed in European patent No. 0341745 B1 incorporated herewith by reference;

deacetylates of HA: these derive from the deacetylation of the N-acetyl-glucosamine unit with a percentage of deacetylation preferably between 0.1 and 30% while all the carboxylic groups of HA can be salified with organic and/or inorganic bases, as illustrated in the following structure (A):

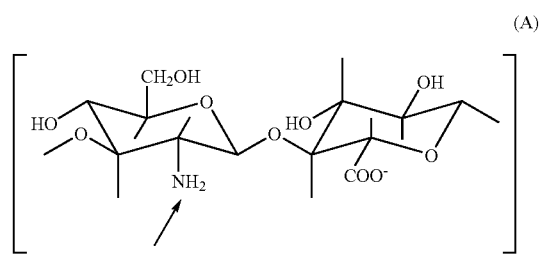

Deacetylates of HA are disclosed in International Patent Application No. WO 02/18450 we incorporate herewith by reference;

Hyoxx™: percarboxylated HA derivatives obtained by oxidation of the primary hydroxyl of the N-acetyl-glucosamine unit with a degree of percarboxylation of between 1 and 100%, preferably between 25 and 75%. All the carboxylic groups of HA can be salified with organic and/or inorganic bases as illustrated in the following structure (B):

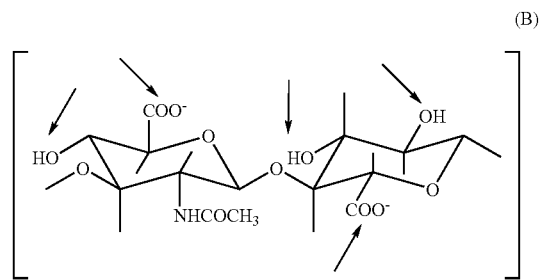

Percarboxylated HA derivatives are disclosed in US Patent Application No. US2003181689.

Moreover, the present compounds wherein a taxane, and in particular paclitaxel, is covalently bounded to an HA ester, may be obtained by starting from molecules of chemically unmodified HA and, only after synthesis with the chemotherapy drug, modifying the HA by esterifying it with all the alcohols listed above for the Hyaff® products, or by forming inner esters as in the case of ACP® (see Example 8).

The previously listed HA derivatives, that are particularly important in the process of synthesis of the prodrug HA-taxane, and in particular of the prodrug HA-paclitaxel, are the deacetylated and sulphated derivatives because at the same percentages of paclitaxel bound to previously unmodified hyaluronic acid, they render the final product more soluble in the bloodstream.

It is known that, by means of the CD44 membrane receptor, HA modulates many different processes relative to cell physiology and biology such as the proliferation, differentiation and locomotion of cancer cells and other cells.

Scientific literature has recently demonstrated the efficacy of HA against cancer, when HA is injected as such directly into the cancer growth. It has proved to be able to determine the complete regression of 30% of tumours (HerreraGayol, A. et al., *Experimental and Molecular Pathology*, 2002, 72: 179-185).

It is also known that HA can be associated with any chemotherapy drug to prepare many different pharmaceutical compositions, as it is able to act as a second antineoplastic agent that synergically enhances the anticancer action of the drug associated with it (International Patent Application No. WO 01/47561); alternatively, HA is claimed as an anticancer drug to be administered on its own in various clinical protocols for the reduction/regression of the cancer growth (International Patent Application No. WO 97/40841).

The present taxane covalently bounded to HA or HA derivatives, as above said, differs from all the formulations of taxanes, in particular the covalent bound of paclitaxel with HA or HA derivatives, optionally by means of a spacer, renders the paclitaxel soluble in water, without diminishing its pharmacological efficacy, Indeed, the in vivo experiment described in Example 1 clearly demonstrates the same anticancer efficacy of the present conjugated paclitaxel and non-conjugated paclitaxel, when same doses are administered.

Moreover, HA-paclitaxel can present unexpected pharmacological properties that are different from those of the non-conjugated paclitaxel, especially in the case of certain types of tumour.

Indeed, Example 2 clearly demonstrates that the present ester derivative of HA bounded to paclitaxel has a new antineoplastic pharmacological activity: in the model of in vitro cytotoxicity described hereafter, the present HA-paclitaxel shows surprising anticancer activity that is far superior to that exerted by non-conjugated paclitaxel alone.

This new antineoplastic property means that the present taxanes, in particular the paclitaxel, conjugated to HA or HA derivatives, can be used for the preparation of pharmaceutical compositions useful as a chemotherapy drug, not only for the treatment of all the forms of tumour for which Taxol® is administered, but also for other forms of tumour not normally treated with Taxol®, such as cancer of the stomach and liver, cancer of the colon, melanoma and leukaemia. Moreover, it can be used in systemic autoimmune disorders such as rheumatoid arthritis, systemic lupus erythematosus, autoimmune glomerulonephritis and, lastly, Hashimoto's thyroiditis.

The use of the present products in a new pharmacological therapy for the above said pathologies is possible because the new HA-paclitaxel compound reduces the systemic toxicity of Taxol®thus increasing the therapeutic efficacy of the drug itself, since it is:
  water-soluble;
  not associated with Cremophor® EL and is therefore free from the toxic effects that this produces;
  equally efficacious at doses decidedly lower than (or equal to) those normally used in clinical protocols.

Also known is the use of paclitaxel as a drug to be used to inhibit the process of restenosis that generally follows angioplasties (prevalently arterial), coronary bypass and organ transplants.

The present taxanes, and in particular the paclitaxel, covalently bounded to HA or HA derivatives can also be used for the prevention of restenosis or they can be used to form an inner coating for stents and devices implanted after the above-listed vascular operations, as it has proved possible to bind it chemically to the surface of said stents or to adsorb it easily to them.

In either case, the residence time of the present products on the surface of the stent, and consequently its gradual release into the bloodstream, is greater than that of non-conjugated paclitaxel because the chemical-physical characteristics of HA favour a progressive, slow but continuous release of Taxol® from the surface of the device.

The pharmaceutical compositions comprising the present taxanes covalently bounded to HA or HA derivatives can be administered systemically (by the intravenous or arterial, intramuscular, intraperitoneal, subcutaneous or oral routes), it can be used for topical application (by transdermal absorption), or it can be administered directly into the cancer site by means of injection. HA or a derivative thereof covalently bound to paclitaxel, can also act as an anticancer drug per se.

In the following Example 3, the Applicant demonstrates how treatment of experimentally-induced tumour growths in nude mice with the cross-linked derivative of HA, ACP®, determines a significant regression of the tumour compared to the non-treated controls.

The Applicant therefore describes for the first time a new role for HA and the derivatives thereof that constitute the present products taxane-HA or taxane-HA derivative, as antineoplastic agents and their relative uses in the field of oncology. The present taxanes covalently bounded to HA or HA derivatives can, moreover, be associated with various biologically and pharmacologically active molecules such as, for example, steroids, hormones, proteins, trophic factors, vitamins, non-steroid anti-inflammatory drugs, chemotherapy drugs, calcium-antagonists, antibiotics, antiviral agents, interleukins and cytokines such as Interferon.

In this way, it is possible to obtain many different associations of the above said drugs and relative different pharmaceutical compositions comprising the taxanes of the invention.

The present Invention also relates to the process for preparing the present taxanes, in particular paclitaxel, covalently bounded to HA or HA derivatives; the present products may be achieved by the following processes:

1) by an indirect synthesis that involves the introduction of a spacer between the taxane and HA or HA derivative, or
2) by a direct synthesis between the taxane and HA or HA derivative.

The functional groups of HA or HA derivatives that can react with the taxane directly or indirectly by means of a spacer, are the following:
1) hydroxyl groups;
2) carboxyl groups;
3) amino groups of deacetylated HA.

The spacer may be for example selected from the group consisting of an aliphatic or araliphatic chain, linear or branched, substituted by one or more groups selected from hydroxyl, carboxyl or carbonyl groups, epoxides, acyl chlorides, mercaptans, nitryls, halogens, anhydrides, isocyanates and isothiocyahates, and amino groups.

Amongst the possible spacers, the bromides of carboxylic acids having from 2 to 18 carbon atoms are preferable, and in particular those having from 3 to 10 carbon atoms; more preferred are 3bromopropionic acid and 4bromobutyric acid. The synthesis reaction between the functional hydroxylic groups of HA (or the derivatives thereof) and a taxane component such as paclitaxel, can be achieved by a process of indirect or direct synthesis.

Indirect synthesis may lead to the formation of the following types of covalent bond between the spacer and HA or HA derivatives:

ester bond:
  involving the carboxyl function of a suitably chosen spacer that is activated by an activating agent such as, for example, a carbodiimide (Scheme 1 below);
  involving the hydroxyl groups of HA or HA derivative that are brominated or substituted with a tosyl group with subsequent nucleophilic substitution by the carboxyl of the suitably chosen spacer (Scheme 2 below); or
  involving the anhydride function of a suitably chosen spacer (Scheme 3 below).

Scheme 1-2-3

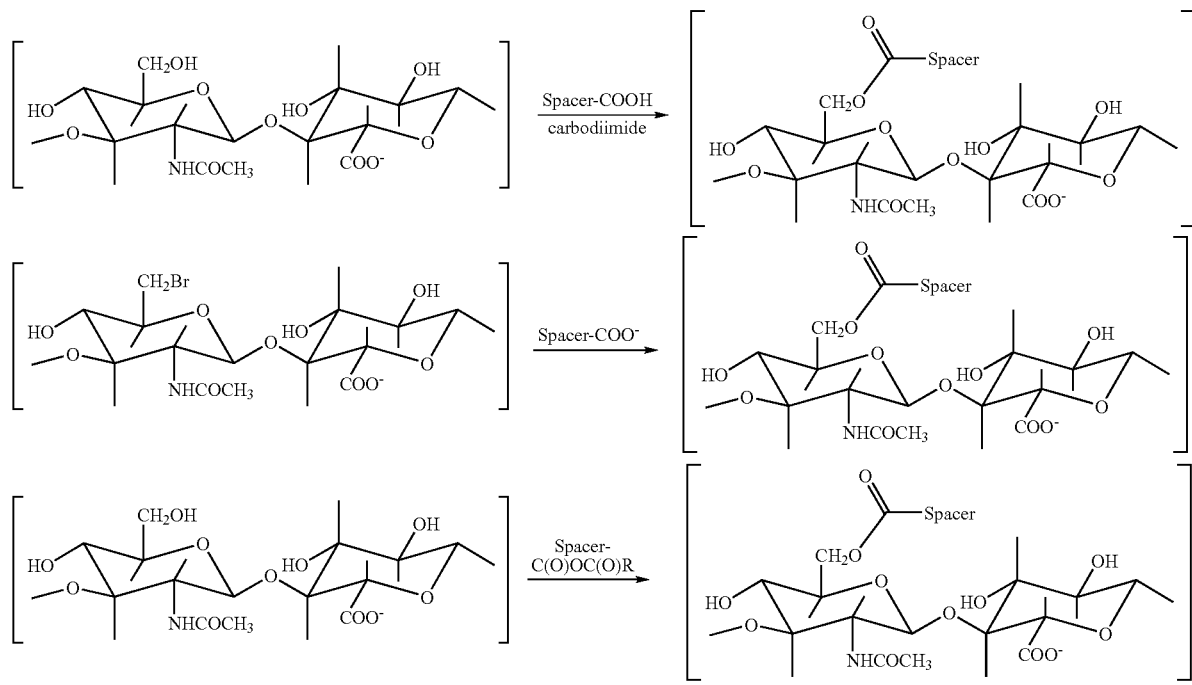

urethane or thiourethane bond:
  involving the amino group of a suitably chosen spacer (Scheme 4 below); or
  involving the isocyanate or isothiocyanate function of a suitably chosen spacer (Scheme 5 below).

Scheme 4-5

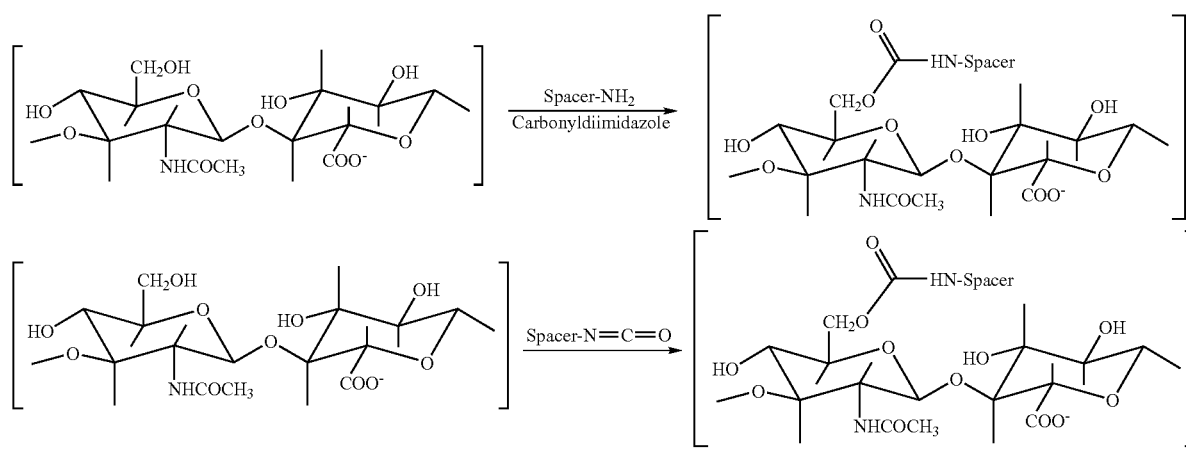

ether bond:
  involving the epoxy function of the (suitably chosen) spacer (Scheme 6 below);
  involving the hydroxyl groups of HA or HA derivative that are brominated or substituted by a tosyl group, with subsequent nucleophilic substitution by the hydroxyl group of a suitably chosen spacer (Scheme 7 below).

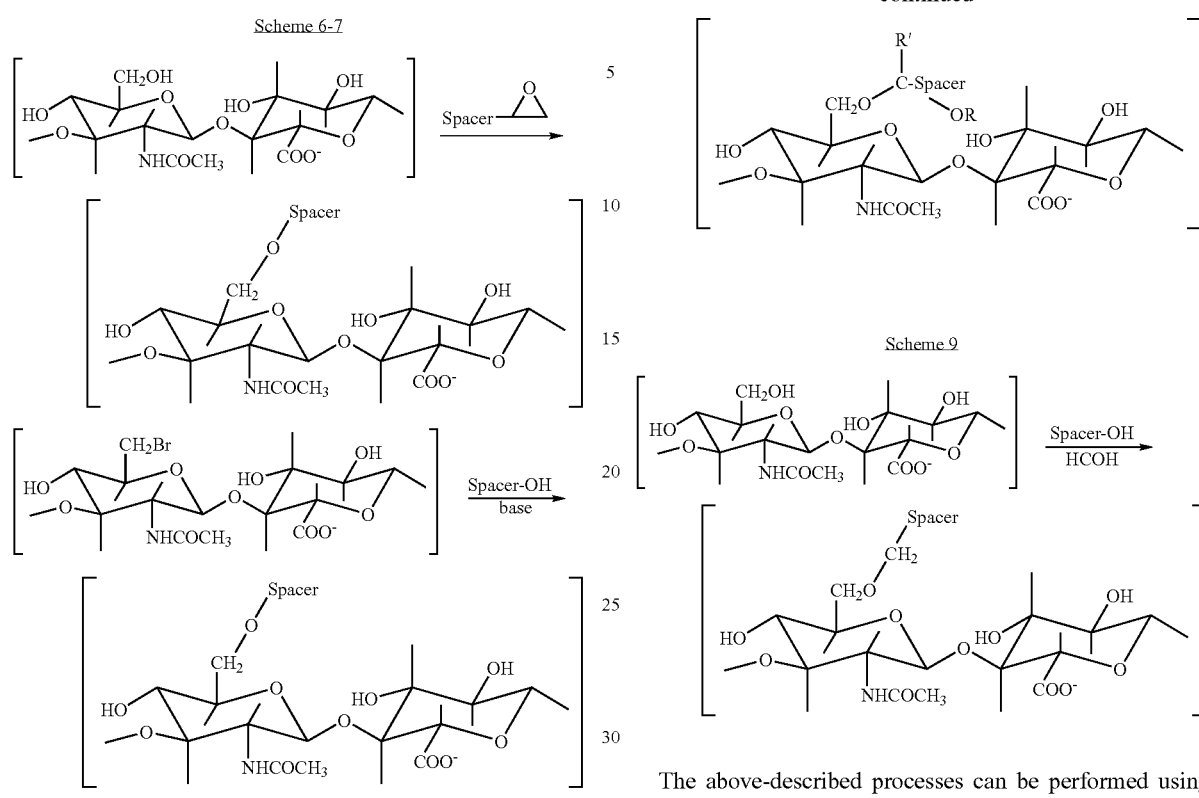

acetal or ketal bond:
  involving the aldehyde and/or ketonic group of the suitably chosen spacer (Scheme 8 below);
  involving the hydroxyl group of the suitably chosen spacer and requiring the presence of a simple carbonyl compound, such as formaldehyde (Scheme 9 below).

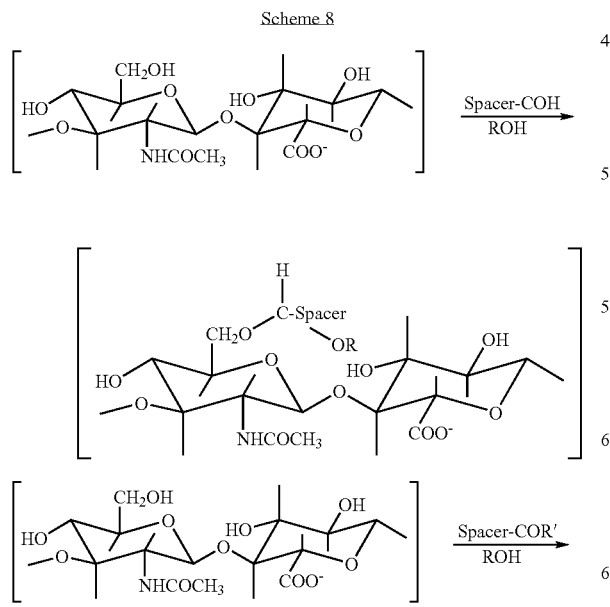

The above-described processes can be performed using agents activating of the hydroxyl group of HA or HA derivatives, for example selected from the group consisting of carbonyldiimidazole and di-(N-succimidyl)carbonate.

The direct synthesis reaction between the hydroxyl groups of HA or HA derivatives and a taxane such as paclitaxel, may lead to the formation of the following type of covalent bond:

acetal bond:
  involving the hydroxyl group of the taxane and the hydroxyl groups of HA or HA derivatives, which are covalently bounded by addition of a simple carbonyl compound such as formaldehyde (Scheme 10)

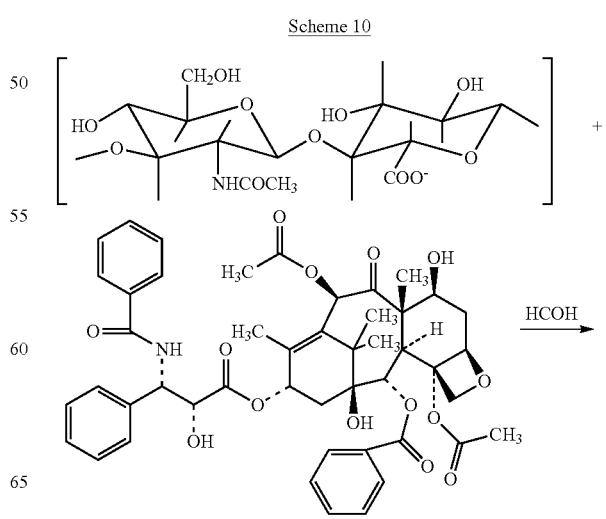

-continued

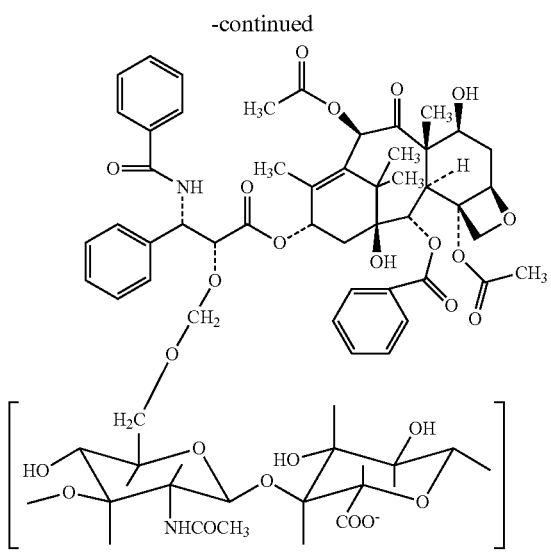

The reaction between the carboxyl groups of HA or HA derivatives and a taxane such as paclitaxel, can be achieved by a process of direct or indirect synthesis.

Indirect synthesis may lead to the formation of the following types of covalent bond between the spacer and HA or HA derivatives:

ester bond:
- the carboxylic group of the suitably chosen spacer, such as 4-bromobutyric acid, is activated by an activating agent such as a carbodiimide and thus made suitable for synthesis with the hydroxyl group of the taxane (preferably that on carbon at C2′), such as paclitaxel. Subsequently, by direct contact in an anhydrous solvent with a quaternary ammonium salt, in particular the tetrabutylammonium (TBA) salt of HA or HA derivative, a nucleophilic substitution is obtained of the carboxyl of HA or HA derivative to the bromine of the spacer. In this way an ester bond is formed between HA or HA derivative and the spacer, in turn bounded to paclitaxel. Alternatively, the nucleophilic substitution of the carboxyl group of HA or HA derivative to the bromine of the spacer may occur before the bond between the spacer itself and the taxane (Scheme 11 below).
- by using the activating agents of the carboxyl group of HA or HA derivative such as a carbodiimide, it is possible to obtain an ester bond between said group and the hydroxyl function of the (suitably chosen) spacer, previously or subsequently bound to paclitaxel (Scheme 12 below).

Scheme 11-12

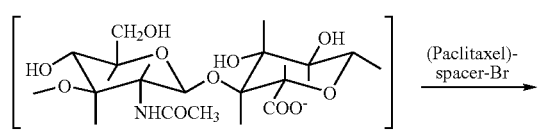

-continued

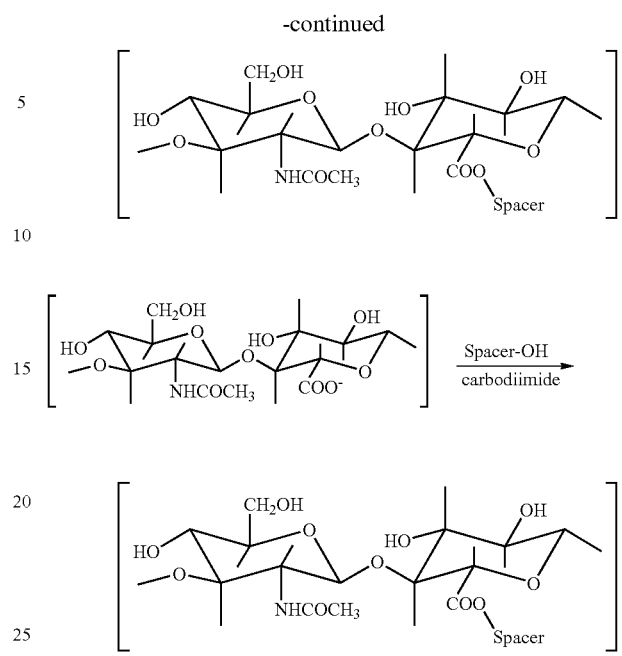

amide bond:
- activation of the carboxyl groups of HA or HA derivatives by an activating agent, enables a linkage with the amino group of the suitably chosen spacer, with the exception of all the hydrazides, previously or subsequently bound to a taxane such as paclitaxel (Scheme 13 below).

Scheme 13

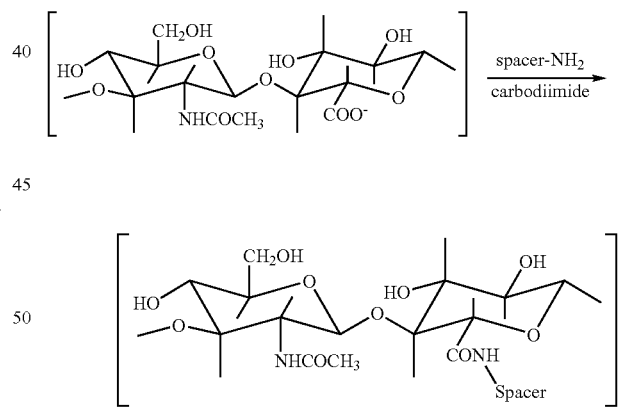

Direct synthesis can lead to the formation of the following types of covalent bond:

ester bond:
- the activation of the carboxyl groups of HA or HA derivative by an activating agent, enables its linkage with the hydroxyl group of the taxane (Scheme 14 below);
- activation of the hydroxyl of the taxane component by the activating agent enables its linkage with the carboxylic function of HA or a derivative thereof (Scheme 14);

Scheme 14
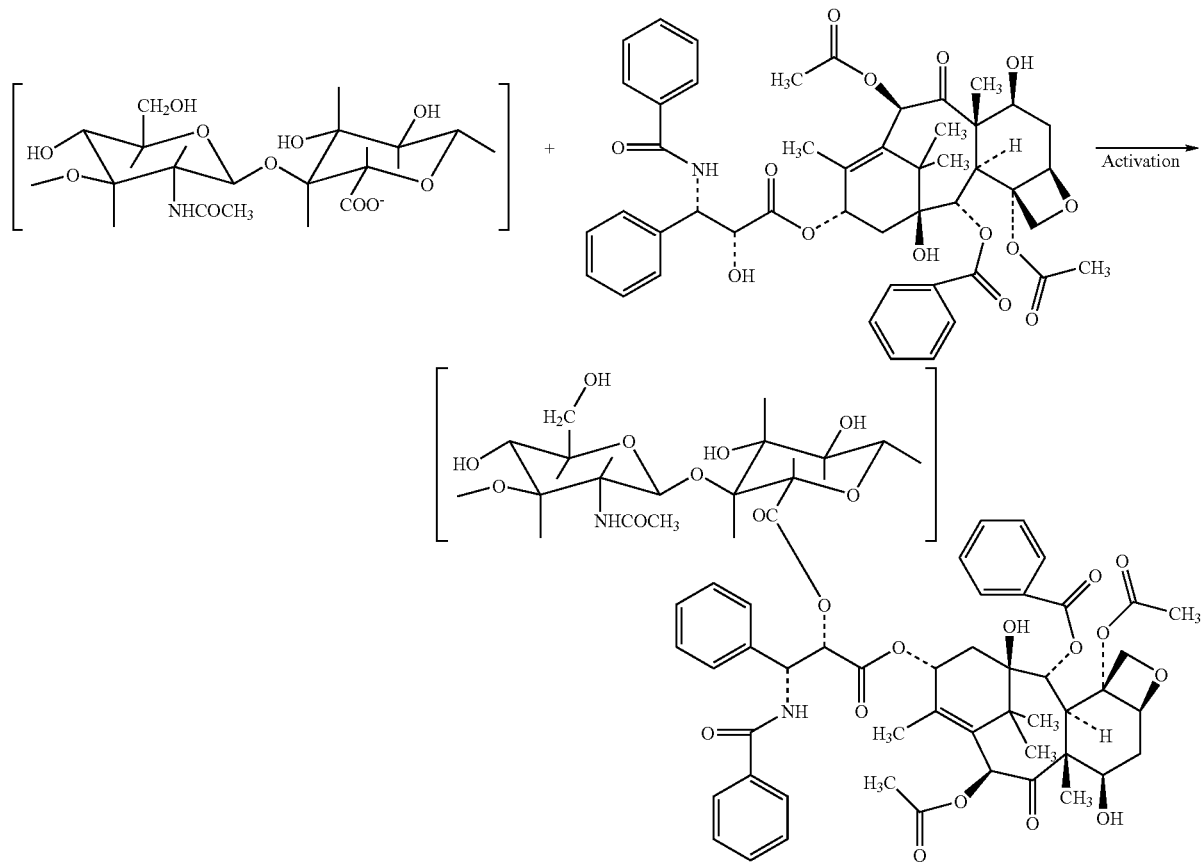
the following type of bond requires the bromide or tosylate of the taxane. Said bond is prepared by nucleophilic substitution of the bromide or the tosyl group by the carboxyl group of HA or HA derivative (Scheme 15).

Scheme 15
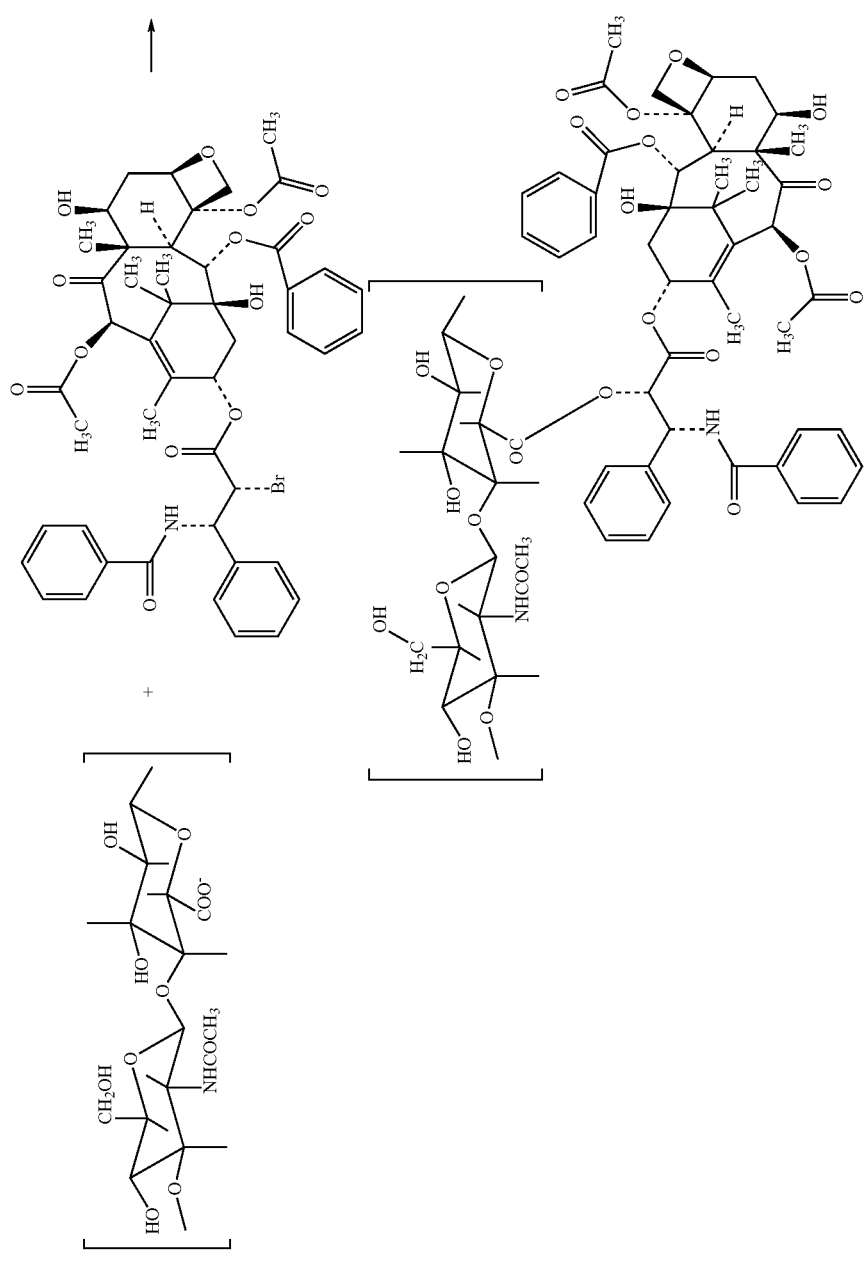

The synthesis reaction between the amino groups of deacetylated HA and a taxane component such as paclitaxel can come about by a process of indirect or direct synthesis.

Indirect synthesis can lead to the formation of the following types of covalent bond between the spacer and HA:

amide bond:

involving the carboxylic group of a suitably chosen spacer (Scheme 16);

Scheme 16 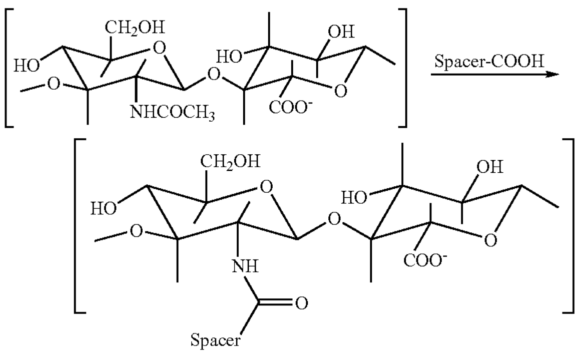 urethane or thiourethane bond:

involving the hydroxyl or thiolic group of a suitably chosen spacer (Scheme 17).

Scheme 17

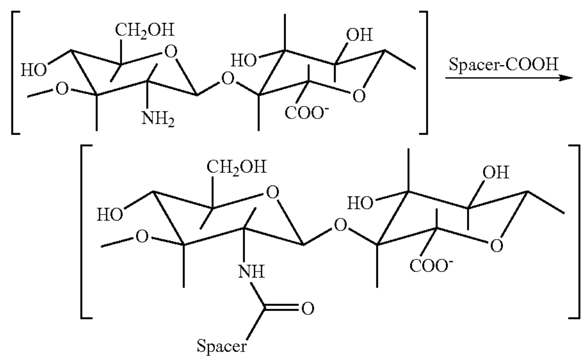

Direct synthesis can lead to the formation of the following type of covalent bond:

urethane bond:

involving the hydroxyl group of the taxane and the amino function of deacetylated HA (Scheme 18).

Scheme 18

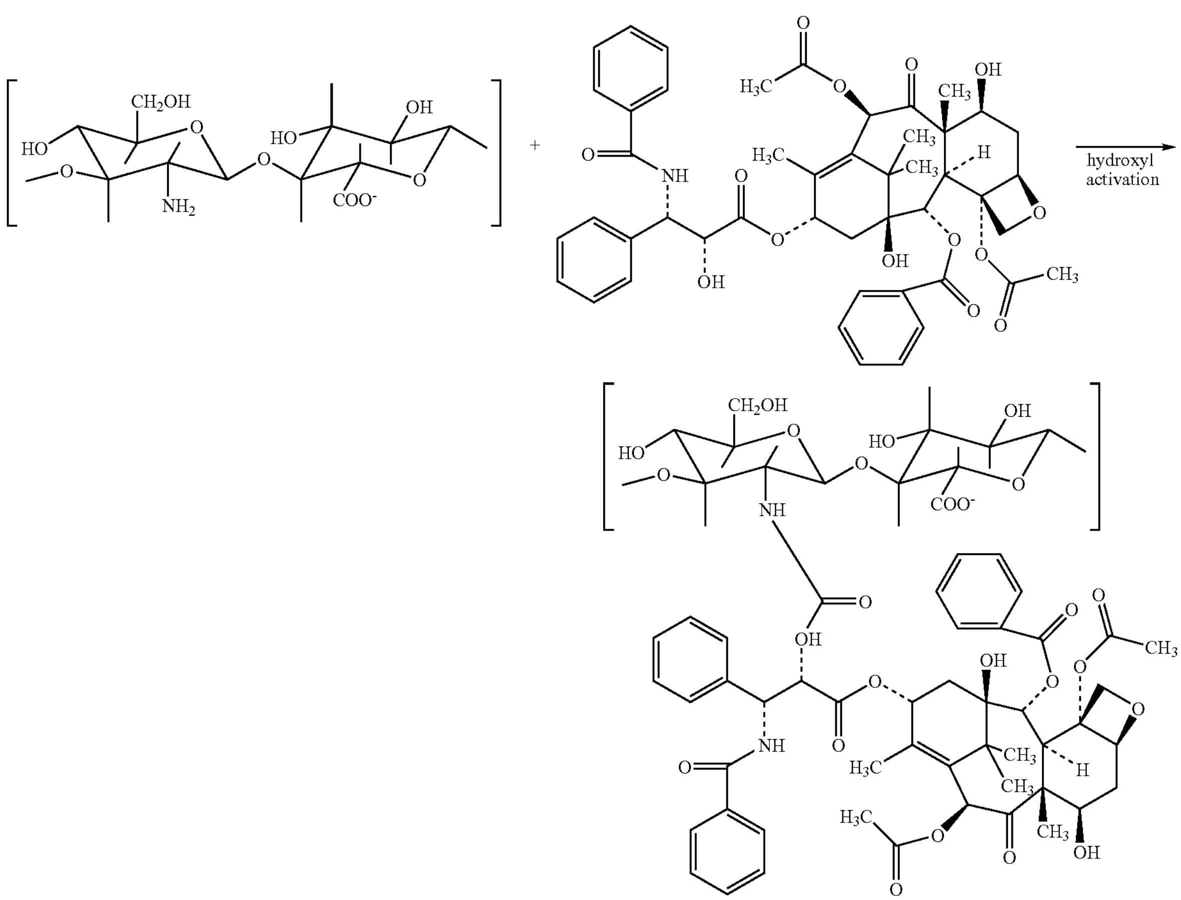

In the same way, the bond involving the spacer and a taxane such as paclitaxel, may be of ester (Scheme 19), urethane or thiourethane (Scheme 20), acetal or ketal type (Scheme 21) and may require the presence of an activating agent especially for the ester and urethane bonds.
Scheme 19
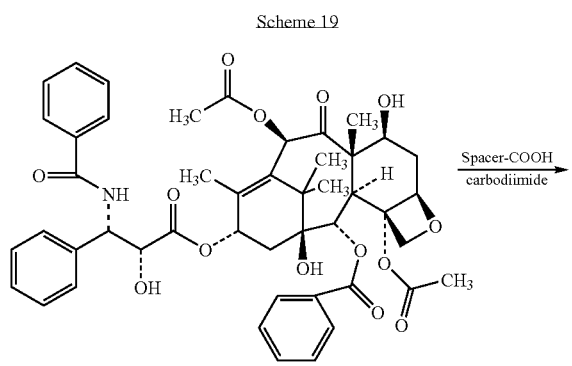
Scheme 20
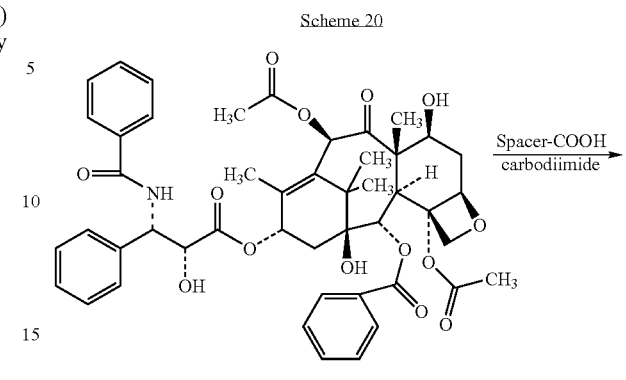
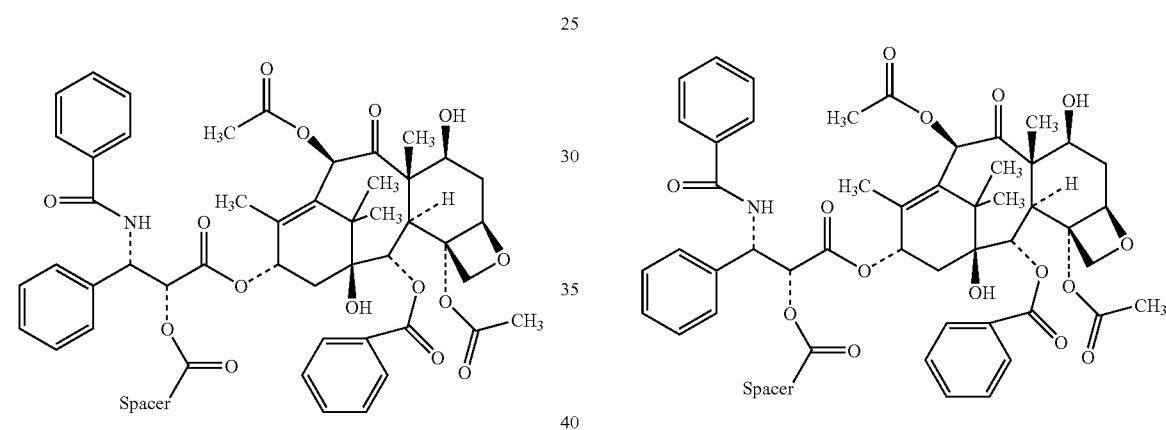
Scheme 21
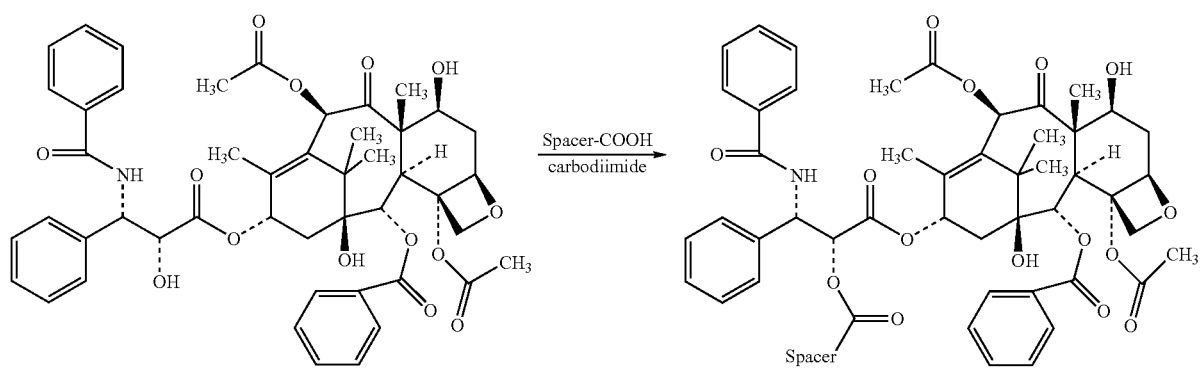

The spacer can be bound to the taxane such as paclitaxel before or after its linkage with the functional groups of HA or HA derivatives, depending on the type of functional groups of the suitably chosen spacer.

The percentage of direct or indirect linkage of the taxane, such as paclitaxel, to HA or HA derivative may vary between 0.1% and 100% and preferably between 0.1% and 35%.

The following examples are given to provide non-limiting illustrations of the present invention.

EXAMPLE 1

Effect of the New Ester Derivative of HA with Paclitaxel in Nude Mouse After Implant of Neoplastic Cells For this experiment, we used human ovary adenocarcinoma cells, OVCAR-3 cells, in immunodepressed nude mice belonging to the Athymic CD-1 species.

Each mouse was inoculated by the intraperitoneal route with $5 \times 10^6$ cancer cells.

Experimental Design

Test drugs:

Taxol®, 5 animals treated

HYTAD1p20: ester derivative of HA covalently bound to paclitaxel with 16% of esterification of the carboxyl (w/w). The molecular weight of the HA used for synthesis of this new drug was 200,000 Da (see Example 7 for details of its preparation). Five animals were used for this drug too.

Treated animals: 10 animals were first inoculated with OVCAR-3 cells. Five were used for the experiment with Taxol® and another five for the experiment with HYTAD1p20:

all ten animals subsequently received, by intraperitoneal injection, 3 doses of pharmacological treatment (on the $6^{th}$, $13^{th}$ and $20^{th}$ days after inoculation of the cancer cells), equal to 20 mg/kg body weight of Taxol® or 125 mg/kg body weight of HYTAD (corresponding to 20 mg/mouse of paclitaxel).

Control animals: 5 animals were first inoculated with the cancer-inducing suspension of OVCAR-3 cells, after which they did not receive any treatment.

Determination of the Survival Curve

The survival curve was calculated from the date of intervention to the $92^{nd}$ day after inoculation of the cancer cells into the peritoneum.

Results: the results obtained are illustrated in FIG. 1.

Three control animals developed adenocarcinoma of the ovary and died between the $70^{th}$ and $75^{th}$ days after inoculation of the cancer cells.

On the $92^{nd}$ day after intervention, the last day of the experiment, none of the animals that had received pharmacological treatment with paclitaxel or HYTAD had died.

EXAMPLE 2

In vitro Experiment

The aim of the in vitro experiment was mainly to define the activity profile of the new ester derivatives of HA bound to paclitaxel and to assess/compare the antineoplastic activity of the HYTAD derivatives vs paclitaxel, thus determining their pharmacological potential compared to the antineoplastic drug.

Experimental Design:

Test products:

Taxol®: reference product

HYTAD1p20—HYTAD2p20—HYTAD2p10: ester derivatives of HA covalently bound to paclitaxel with 16% of esterification of the carboxyl (w/w) (in the case of HYTAD1p20, the molecular weight of the HA used in the synthesis of this new drug is 200,000 Da) (see Example 7 for details of its preparation) or 22% (in the case of HYTAD2p20, the molecular weight of the HA used is 39,000 Da), or 6.8% (in the case of HYTAD2p10, the molecular weight of the HA used is 39,000 Da).

Cell Lines

Cell Lines of Human Origin

Four cell lines of human breast cancer were used. All four of the test cell strains normally respond to paclitaxel and express the receptor CD44 apparently with the same amplification.

MCF-7

MDA-MB-231

MDA-MB-468

SKBR-3

Experimental Protocol:

1) the test cell line is plated at a concentration of 3,000 cells per well, on a flat-bottomed, 96-well plate;
2) 24 hours later, the cells are supplemented with the test solutions suitably diluted in culture medium;
3) after another 72 hours, the cells are tested by colorimetry with 3-(4,5-Dimethyl-2-thiazolyl)-2,5-diphenyl-2H-tetrazolium bromide (MTT); by assessing cell viability, this test also reveals the different sensitivity of the cells to the test drug. This is possible because mitochondrial dehydrogenase is able to reduce the tetrazolium salts (yellow) into blue formazan crystals. The greater or lesser intensity of colour is assessed by spectrophotometry (Dezinot, F. et al., J. Immunol. Methods, 1986, 22 (89): 271-277).

Results

Figure 2:
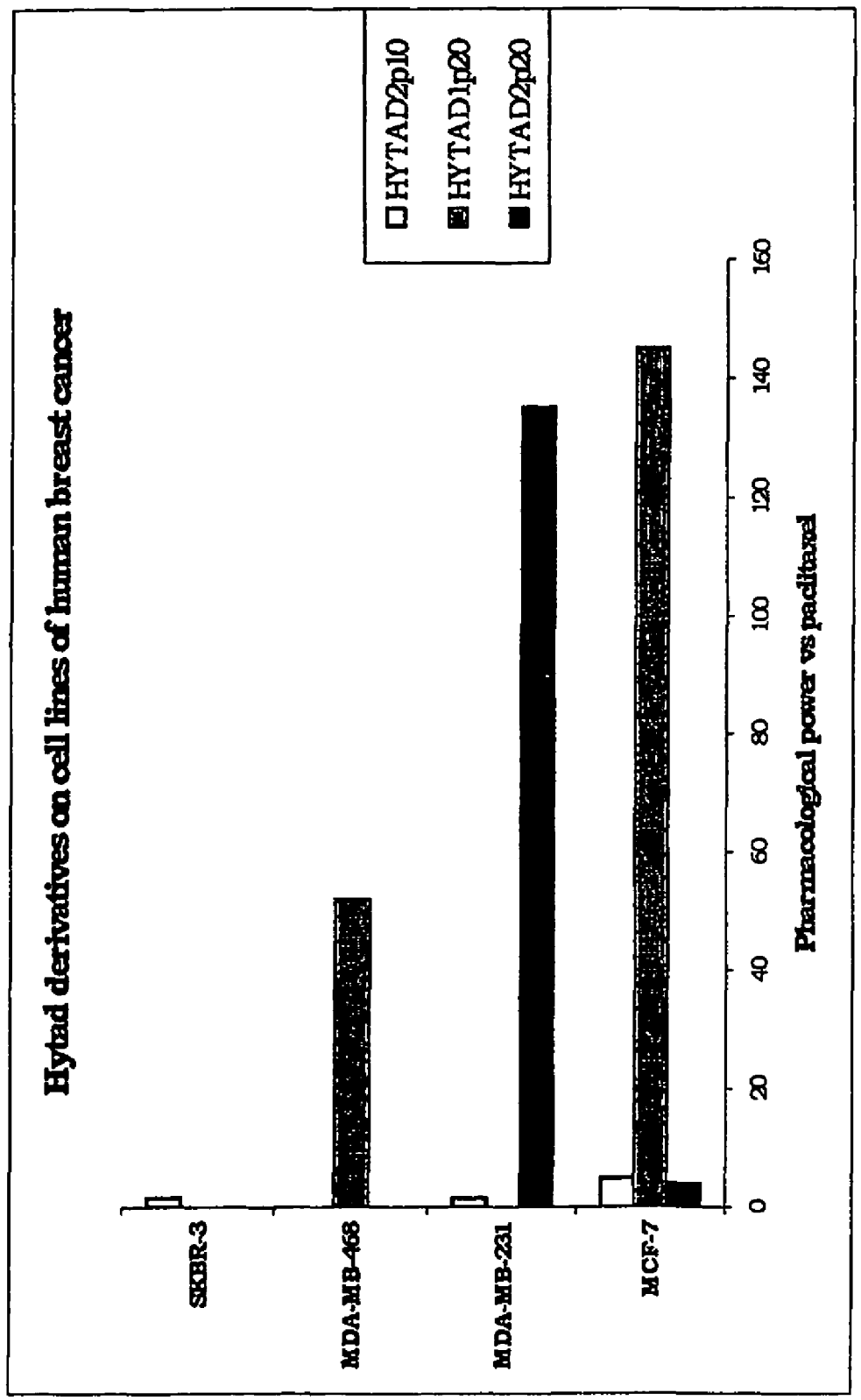
FIG. 2 shows the pharmacological power expressed as IC50 and resulting from experiments in Example 2, of the paclitaxel covalently bounded to ester derivatives of HA having 16% esterification (grey histogram), 22% of esterification. (black histogram) and 6.8% of esterification (white histogram) for four cell lines of breast cancer, vs. the reference product paclitaxel.

Hereafter we report, in table and graph form in FIG. 2, the results obtained in terms of $IC_{50}$ (the concentration of drug necessary to inhibit cell growth by 50% with regard to the test product and the different cell lines used).

In FIG. 2, the axis of abscissas represents the pharmacological power, expressed as $IC_{50}$ and calculated as the ratio between the molar concentrations, vs the reference product (paclitaxel) which is conventionally taken to have a value of nil. Consequently, the dashes indicate a pharmacological power that is greater than the reference product.

$IC_{50}$ (expressed as nM or µM of paclitaxel or its HYTAD derivatives in the culture medium)

| Cell lines | Taxol ® | HYTAD2p20 | HYTAD1p20 | HYTAD2p10 |
|---|---|---|---|---|
| Breast cancer cell lines | | | | |
| MCF/7 | 3.5 nM | 0.86 nM | 0.024 nM | 0.68 nM |
| MDA/MB231 | 0.35 nM | 2.58 nM | — | 0.24 µM |
| MDA/MB468 | 9.4 nM | — | 0.18 nM | — |
| SKBR/3 | 0.23 nM | — | — | 0.14 nM |

Conclusions

As reported in the literature, all the cell lines used are sensitive to taxol, a drug mainly used to treat metastatic carcinoma of the breast and of the ovary. As regards the breast cancer cell lines, the various HYTAD proved to be considerably stronger than paclitaxel, with a factor of +150 with regard to HYTAD1p20 on cancer cell line MCF-7.

EXAMPLE 3

Effect of ACP® Gel in Nude Mice After Implantation of Neoplastic Cells.

For this experiment, we used human colic carcinoma HT29 cells In immunodepressed nude mice belonging to the Athymic Nude-nu (nu/nu) species. Each animal was anaesthetised and 0.3 ml of an HT29 cell suspension was injected into its peritoneal cavity at a concentration of 166,000 cells/ml. Thus, each mouse received 50,000 cancer cells.

Experimental Design:

Treated animals: 113 animals were first inoculated with HT29 and immediately afterwards they received a single dose of treatment equal to 0.2 ml of ACP gel 40 mg/ml;

Control animals: 117 animals were inoculated with HT29 cancer cell suspension but received no treatment.

Figure 3:
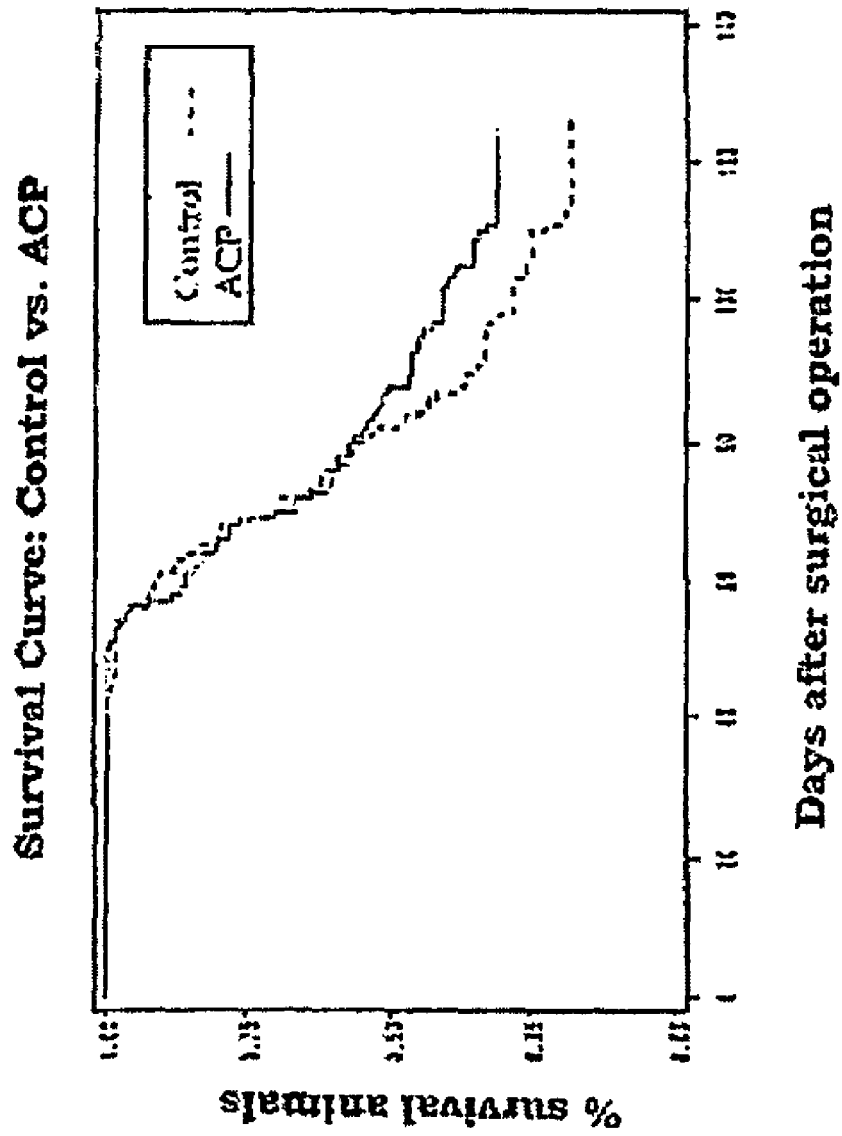
FIG. 3 shows the percentage of survival after implantation of neoplastic cells as described in Example 3, in control mice (broken line) and in mice who received ACP® gel (continuous line).

Survival curve: the survival curve was calculated from the day of inoculation up to the day of death. Deaths were either ascertained or caused by the sacrifice of animals whose weight had dropped by more than 20% of their starting weight, and in the case of hemoperitoneum indicating diffuse metastases. The percentage of survival in the two groups was determined daily and expressed as a graph to obtain the curve reported in FIG. 3.

The experiment lasted 120 days, after which all the surviving animals were sacrificed and examined necroscopically to check for the presence of abdominal tumours.

Results: 32 animals out of 230 had not developed any notable neoplasia. 22 of these animals belonged to the group of mice treated with ACP® gel, 10 to the control group.

ACP® gel: 19.5% of the treated animals did not develop neoplasia;

Control: 8.5% of the control animals did not develop neoplasia.

EXAMPLE 4

Preparation of HA with a Molecular Weight of Between 5,000 and 10,000 Daltons (for Possible Synthesis of HA-paclitaxel with Low-molecular-weight HA)

2.40 g of sodium HA with a molecular weight of 990,000 Da is dissolved in 240 ml of a solution of 0.15M NaCl. This is then supplemented with 7.9 ml of a 14% solution of NaOCl. At a constant temperature of +4° C., the solution is sonicated for 120 minutes at a frequency of 20 Hz and at 150 W. Once the reaction is complete, the pH is adjusted to 6.5 with 0.1N HCl and the solution is then precipitated in 1.000 ml of a 2:1 mixture of methanol-acetone. The product is collected by filtration and vacuum-dried for 48 hours at 45° C. 1.65 g of sodium salt is thus obtained. High pressure liquid chromatography (HPLC)-GPC analysis reveals that the fraction of HA obtained has a mean molecular weight (MW) of 5,850, a mean numerical molecular weight (MN) of 3,640 and a polydispersity index of 1.61.

EXAMPLE 5

Preparation of an Ester Derivative of HA Bound to Paclitaxel With Esterification of the Carboxyl of about 4% w/w 51 mg of paclitaxel is dissolved in $CH_2Cl_2$ and the solution is supplemented with 104 mg of 1-(3-dimethylaminopropyl)-3-ethylcarbodiimide (EDC) and 20 mg of 4-bromobutyric acid. Subsequently, the solution is partitioned in water. After eliminating the carbodiimide and bromide residues, the reaction solvent is dried with anhydrous sodium sulfate and eliminated with a rotary evaporator. 21 mg of product thus obtained is dissolved in n-methyl-pyrrolidone (NMP) and added to a 20 mg/ml solution of HA salified with tetrabutylammonium. (TBA) in NMP (200 mg in 10 ml NMP). After seven days' reaction at ambient temperature, the solution is diluted with 5 ml of water and 1 ml of saturated NaCl solution. The solution thus obtained is stirred for 1 hour to enable the exchange of sodium with the TBA ion. Subsequently, ethanol is slowly added a drop at a time and the filamentous product thus obtained is dissolved in water, dialysed and lastly freeze-dried.

EXAMPLE 6

Preparation of an Ester Derivative of HA With Paclitaxel With Esterification at the Carboxyl of about 10% w/w As in Example 5, 308.7 mg of paclitaxel dissolved in 15 ml of dichloromethane is supplemented with 117.2 mg of 4-bromobutyric acid and 614.1 mg of EDC. Subsequently, water is added to the solution to eliminate all the bromide and carbodiimide. The organic solution thus obtained is supplemented with sodium sulphate to dehydrate it while the solvent is eliminated with a rotary evaporator. Finally, 363 mg of intermediate product is obtained.

175 mg of intermediate product thus obtained is added to 1 g of HA-TBA dissolved in anhydrous NMP. The solution is stirred at ambient temperature for 7 days, after which 20 ml of water and 4 ml of a saturated NaCl solution are added. It is stirred for 1 hour to enable the exchange of sodium with the TBA ion. Subsequently ethanol is slowly added a drop at a time and the filamentous product this obtained is dissolved in water, dialysed and lastly freeze-dried.

EXAMPLE 7

Preparation of an Ester Derivative of HA With Paclitaxel With Esterification at the Carboxyl of about 16% w/w 164 mg of intermediate product, obtained according to the procedure described in the previous examples No. 5 and 6, is added to a solution of 680 mg of HA-TBA dissolved in 25 ml of anhydrous NMP. After 7 days' reaction at ambient temperature, the solution is supplemented with 20 ml of water and 4 ml of saturated NaCl solution. After 1 hour, ethanol is slowly added a drop at a time. The product obtained is collected by filtration and dissolved in water, dialysed and, when the conductibility of the dialysis solution has dropped below 10 µS, it is frozen. The frozen solution is then freeze-dried.

EXAMPLE 8

Preparation of an Ester Derivative of HA With Paclitaxel With Esterification at the Hydroxyl of about 10% w/w 102.6 mg of paclitaxel is dissolved in 5 ml of dichloromethane and the solution is supplemented with 20.4 mg of succinic anhydride. Three hours later, the solvent is eliminated by evaporation using a rotary evaporator. The product thus obtained is dissolved in 5 ml of dimethyl sulphoxide (DMSO) with low water content, and 27.3 mg of dicyclohexyl-carbodiimide is added. About 5 minutes later, the solution is supplemented with a solution of HA-TBA, obtained by dissolving 327 mg of polymer in 15 ml of DMSO with low water content. The solution is stirred at ambient temperature for about 24 hours. Subsequently, a few ml of water and 3 ml of a saturated NaCl solution are added to the solution. After 1 hour it is precipitated by adding ethanol. The filamentous product collected by filtration is dissolved in water, dialysed and lastly freeze-dried.

EXAMPLE 9

Preparation of an Ester Derivative of HA With Paclitaxel With Esterification at the Carboxyl of about 4% w/w 510.1 mg of paclitaxel dissolved in 6 ml of dichloromethane is supplemented with 95.4 mg of 3-3 bromopropionic acid and 525.0 mg of EDC. Subsequently, water is added to the solution to eliminate the bromide and the carbodiimide by partitioning, while 10 volumes of water are used to eliminate the reagents. The organic solution is supplemented with sodium sulphate to dehydrate it and the solvent is eliminated with a rotary evaporator.

155.5 mg of intermediate product thus obtained is added to 1.46 g of HA-TBA dissolved in anhydrous NMP and the solution thus obtained is stirred at ambient temperature for 7 days. Subsequently, 20 ml of water and 4 ml of saturated NaCl solution are added. The solution is stirred for 1 hour to enable the exchange of sodium with the TBA ion. Then ethanol is slowly added a drop at a time and the filamentous product thus obtained is dissolved in water, dialysed and lastly freeze-dried.

EXAMPLE 10

Preparation of an Ester Derivative of Hyaluronic Acid With Esterification at the Carboxyl of about 30% w/w 500 mg of paclitaxel is dissolved in $CH_2Cl_2$ and the solution is supplemented with 397.6 mg of 13-dimethylaminopropyl)-3-ethylcarbodiimide (EDC) and 300.9 mg of 4-bromobutyric acid. Subsequently, the solution is partitioned in water. Once the carbodiimide and bromide residues have been eliminated, the reaction solvent is dried with anhydrous sodium sulphate and eliminated with a rotary evaporator.

The product thus obtained is dissolved in NMP and added to a solution containing ~20 mg/ml of hyaluronic acid salified with TBA in NMP (1.95 g in 100 ml NMP).

After 7 days' reaction at ambient temperature, the solution is diluted with 20 ml of water and 4.5 ml of a saturated NaCl solution. The solution is stirred for 1 hour to enable the exchange of sodium with the TBA ion. Subsequently, ethanol is slowly added a drop at a time and the filamentous product thus obtained is dissolved in water and dialysed and lastly freeze-dried.

EXAMPLE 11

Preparation of the Partial Autocrosslinked Ester (about 10% Substitution) of HA With 8% Paclitaxel w/w 3.10 g of HA salified with TBA is solubilised in 150 ml of DMSO with a low water content at ambient temperature. The solution is then supplemented with 541.0 mg of intermediate paclitaxel obtained according to the method described in examples 5, 6 and 7. Once it has been left to react for 7 days at ambient temperature, the reaction solution is supplemented with 126.5 g of triethylamine and the whole is stirred for 30 minutes.

A solution of 319.5 g of 2-chloro-1-methyl-pyridine iodide in 30 ml of DMSO is slowly added a drop at a time over a 45-minute interval and the mixture is left at 30° C. for 15 hours.

A solution formed by 50 ml of water and 1.7 g of sodium chloride is added and the resulting mixture is poured slowly into 400 ml of acetone while stirring continuously. A precipitate is formed that is filtered and washed three times with 50 ml of acetone water 5:1 and three times with acetone (50 ml). The final product thus obtained is vacuum-dried at 38° C.

EXAMPLE 12

Tests of the Solubility of the HA-paclitaxel Ester Obtained According to Example 5 in a 5% Glucose Solution.

14.6 mg of an HA-paclitaxel product obtained by esterification according to Example 7 (starting from HA with a molecular weight of 200 kDa) with a degree of substitution at the carboxyl of 16.3% w/w, was dissolved in 1 ml of an aqueous solution of 5% glucose. The solution, stirred with a magnetic stirring bar, can be filtered through a 0.20 µm sterility filter fitted on a syringe. The concentration of paclitaxel in the solution is 2.38 mg/ml.

We also attempted to find the maximum concentration of product per ml of 5% glucose aqueous solution. At a concentration of 32.8 mg of HA-paclitaxel product per ml of glucose solution, a viscous solution is obtained with a concentration of paclitaxel of 5.35 mg/ml.

EXAMPLE 13

Tests to Recover Paclitaxel from Human Plasma

A solution is prepared that is constituted by 101.3 mg of HA-paclitaxel In 10 ml of water. The HA-paclitaxel is prepared as described in Example 7.

The recovery test is performed by placing 40 mg of the above described solution in contact with 2 ml of human plasma at 37° C.

To determine the paclitaxel that is released into the plasma by detaching itself from the HA, three contact times were set: 6, 30 and 60 minutes. At the end of each contact interval, the paclitaxel was extracted from the plasma-HA-paclitaxel solution with 3 rinses, each with 1.5 ml of terbutylmethylether (TBME), which were collected together, evaporated to dryness by natural evaporation at 65° C., and resuspended in 400 µl of absolute ethanol to determine the content of the drug in question by HPLC (high pressure liquid chromatography). The results obtained are shown in FIG. 4: after 6 minutes more than 80% of the paclitaxel had become detached from the HA and the percentage had not increased by the later observation times.

The invention being thus described, it is clear that these methods can be modified in various ways. Such modifications are not to be considered as divergences from the spirit and purpose of the invention, and any such modification that may appear evident to an expert in the field comes within the scope of the following claims.

The invention claimed is:

1. A taxane covalently bonded to hyaluronic acid or to a hyaluronic acid derivative, wherein the covalent bond is formed by means of a spacer between hydroxyl groups of the taxane and carboxyl groups of hyaluronic acid or hyaluronic acid derivative and the bond between the carboxylic groups of the hyaluronic acid or derivative thereof and the spacer is an ester bond, with an esterification degree of the carboxyl of 6.8% to 22% (w/w) and wherein the average molecular weight of hyaluronic acid is 39,000 Da to 200,000Da.

2. The taxane according to claim 1, wherein the taxane is selected from between paclitaxel and docetaxel.

3. The taxane according to claim 1, wherein the said taxane is paclitaxel.

4. The taxane according to claim 1, wherein the hyaluronic acid is salified with organic and/or inorganic bases.

5. The taxane according to claim 1, wherein the hyaluronic acid derivative is selected from the group consisting of esters of hyaluronic acid with alcohols of the aliphatic, araliphatic, cycloaliphatic, aromatic, cyclic and heterocyclic series, said esters having an esterification degree equal to or lower than 50%.

6. The taxane according to claim 1, wherein the hyaluronic acid derivative is selected from the group consisting of amides of hyaluronic acid with amines of the aliphatic, araliphatic, cycloaliphatic, aromatic, cyclic and heterocyclic series, said amides having an amidation degree of between 0.1% and 10%.

7. The taxane according to claim 1, wherein the hyaluronic acid derivative is selected from the group consisting of O-sulphated derivatives of hyaluronic acid up to the $4^{th}$ degree of sulphation.

8. The taxane according to claim 1, wherein the hyaluronic acid derivative is selected from the group consisting of inner esters of hyaluronic acid having an esterification degree equal to or lower than 15%.

9. The taxane according to claim 1, wherein the hyaluronic acid derivative is selected from the group consisting of deacetylates of hyaluronic acid, coming from deacetylation of the N-acetyl-glucosamine unit and having a deacetylation degree of between 0.1% and 30%.

10. The taxane according to claim 1, wherein the hyaluronic acid derivative is selected from the group consisting of percarboxylated derivatives of hyaluronic acid obtained from the oxidation of the primary hydroxyl of the N-acetyl-glucosamine unit, having a percarboxylation degree of between 1 and 100%.

11. The taxane according to claim 1, wherein the spacer linking the taxane to hyaluronic acid or hyaluronic acid derivative, is selected from the group consisting of aliphatic or araliphatic chains, linear or branched, substituted with one or more groups chosen from hydroxyl, carboxyl, carbonyl, epoxide, acylchloride, thiol, nitryl, halogen, anhydride, isocyanate, isothiocyanate and amino groups.

12. The taxane according to claim 11, wherein the spacer is selected from the group consisting of carboxylic acids having from 2 to 18 carbon atoms in the aliphatic or araliphatic chain, substituted with bromine.

13. The taxane according to claim 11, wherein the spacer is selected from the group consisting of carboxylic acids having from 3 to 10 carbon atoms in the aliphatic or araliphatic chain, substituted with bromine.

14. The taxane according to claim 11, wherein the spacer is selected from between 3-bromopropionic acid and 4-bromobutyric acid.

15. The taxane according to claim 1, wherein the covalent bond between the taxane and the spacer is a urethane or thiourethane bond.

16. The taxane according to claim 1, wherein the covalent bond between the taxane and the spacer is an acetal or ketal bond.

17. The taxane according to claim 1, wherein the hyaluronic acid or hyaluronic acid derivative enhances the anticancer action of the taxane.

18. The taxane according to claim 8, wherein the inner ester of hyaluronic acid enhances the anticancer action of taxane.

19. The taxane according to claim 1, wherein the hyaluronic acid enhances the anticancer action of taxane.

20. A pharmaceutical composition comprising as the active substance at least a taxane covalently bonded to hyaluronic acid or to a hyaluronic acid derivative as defined in claim 1, in combination with pharmaceutically acceptable excipients and diluents.

21. The pharmaceutical composition according to claim 20, for administration by the oral, intravenous, arterial, intramuscular, subcutaneous, intraperitoneal or transdermal route, or by direct injection into a tumour site.

22. The pharmaceutical composition according to claim 20, for administration by the oral route.

23. The pharmaceutical composition according to claim 20, wherein the hyaluronic acid or the hyaluronic acid derivative is able to release the taxane into the administration site.

24. Medical devices coated by a taxane covalently bonded to hyaluronic acid or to a hyaluronic acid derivative as defined in claim 1.

25. A process for the preparation of a taxane according to claim 1 covalently bonded to hyaluronic acid or hyaluronic acid derivative by means of a spacer having at least an hydroxyl group and linking the carboxyl group of hyaluronic acid or the hyaluronic acid derivative by an ester bond, said process comprising the following steps:
   a) adding an activating agent to a solution containing hyaluronic acid or hyaluronic acid derivative;
   b) adding the spacer possibly optionally previously bound to the taxane, to the solution coming from step a);
   c) optionally purifying the so obtained product, and reacting with the taxane if not previously bonded to the spacer.

26. A process for the preparation of a taxane according to claim 1 covalently bonded to hyaluronic acid or hyaluronic acid derivative by means of a spacer having at least an halogen, and linking the carboxyl group of hyaluronic acid or the hyaluronic acid derivative by an ester bond, said process comprising the following steps:
   a') adding the spacer optionally previously bonded to the taxane, to a solution of hyaluronic acid or hyaluronic acid derivative;
   b') optionally purifying the so obtained product, and reacting with the taxane if not previously bonded to the spacer.

27. A therapeutic method for the treatment of tumours, which comprises administering to a subject in a need for such a treatment a therapeutically effective amount of taxane covalently bonded to hyaluronic acid or to a hyaluronic acid derivative as defined in claim 1.

28. The therapeutic method according to claim 27, wherein the treatment of tumours comprises chemotherapy for breast cancer, cancer of the ovary and/or endometrium, melanoma, lung cancer, cancer of the liver, of the prostate and/or bladder, gastric and/or intestinal cancer, leukaemia and Kaposi's sarcoma.

29. A process for the manufacture of medical devices, comprising the step of coating said medical devices by taxane covalently bonded to hyaluronic acid or to a hyaluronic acid derivative as defined in claim 1.

30. The medical device of claim 24 being a stent.

31. The process according to claim 29, for preparing a stent.

32. The process according to claim 26, wherein said spacer has at least one bromine atom.

* * * * *